United States Patent
Cochran et al.

(10) Patent No.: US 11,842,809 B2
(45) Date of Patent: *Dec. 12, 2023

(54) UPDATING CONFLICTING ENTRIES

(71) Applicant: Global Healthcare Exchange, LLC, Louisville, CO (US)

(72) Inventors: Steve Cochran, Niwot, CO (US); Hatem El-Sebaaly, Houston, TX (US); Mark Wilcox, Louisville, CO (US); Neil Collins, Denver, CO (US); Martin Braure De Calignon, Erie, CO (US); Juhi Jaiswal, Lafayette, CO (US); Scott Witoszynski, Chicago, IL (US)

(73) Assignee: GLOBAL HEALTHCARE EXCHANGE, LLC, Louisville, CO (US)

( * ) Notice: Subject to any disclaimer, the term of this patent is extended or adjusted under 35 U.S.C. 154(b) by 405 days.

This patent is subject to a terminal disclaimer.

(21) Appl. No.: 16/513,515

(22) Filed: Jul. 16, 2019

(65) Prior Publication Data

US 2019/0341143 A1    Nov. 7, 2019

Related U.S. Application Data

(63) Continuation of application No. 15/465,911, filed on Mar. 22, 2017, now Pat. No. 10,403,400.

(51) Int. Cl.
*G16H 40/20* (2018.01)
*G06Q 50/18* (2012.01)

(52) U.S. Cl.
CPC .......... *G16H 40/20* (2018.01); *G06Q 50/184* (2013.01)

(58) Field of Classification Search
CPC .......................... G16H 40/20; G06Q 50/184
See application file for complete search history.

(56) References Cited

U.S. PATENT DOCUMENTS

2002/0010686 A1*  1/2002  Whitesage ......... G06Q 30/0202
                                                          705/80
2002/0169681 A1*  11/2002  Vincent .................. G06Q 10/06
                                                          705/26.41

(Continued)

OTHER PUBLICATIONS

Lu et al. Discovering and Reconciling Value Conflicts for Data Integration. Available at SSRN: <https://ssrn.com/abstract=335580> or <http://dx.doi.org/10.2139/ssrn.335580>. Originally posted Oct. 2002. (Year: 2002).*

Jiang et al. A Framework for Reconciling Attribute Values from Multiple Data Sources. Management Science 53(12):1946-1963. 2007. (Year: 2007).*

(Continued)

*Primary Examiner* — Nathan A Mitchell
(74) *Attorney, Agent, or Firm* — SNELL & WILMER L.L.P.

(57) ABSTRACT

A system and method for reconciling conflicting identifiers from a first entity and a second entity is disclosed. The first entity and the second entity may be associated with a contract for goods to be delivered to an address of an organization. The system and method may include receiving, from the first entity via a first user interface or the second entity via a second user interface, respective files including respective identifiers. The system and method may include updating, in a database, an entry associated with the organization based on the received identifiers such that an organization address identifier assigned by the first entity is associated with an account identifier assigned by the second entity.

20 Claims, 8 Drawing Sheets

(56) References Cited

U.S. PATENT DOCUMENTS

| | | | |
|---|---|---|---|
| 2002/0194008 A1 | 12/2002 | Yang | |
| 2003/0220966 A1* | 11/2003 | Hepper | G06F 16/273 709/203 |
| 2004/0088283 A1* | 5/2004 | Lissar | G06F 16/902 |
| 2004/0133488 A1* | 7/2004 | Daidone | G06Q 40/02 705/34 |
| 2005/0108153 A1* | 5/2005 | Thomas | G06Q 20/12 705/39 |
| 2008/0167901 A1* | 7/2008 | Betz | G06Q 10/10 705/2 |
| 2010/0121752 A1* | 5/2010 | Banigan | G06Q 40/00 705/37 |
| 2010/0305985 A1* | 12/2010 | Wartho | G06Q 20/102 705/7.28 |
| 2011/0071871 A1* | 3/2011 | Wong | G06Q 10/0639 705/7.22 |
| 2011/0258083 A1* | 10/2011 | Ren | G06Q 30/0641 705/27.1 |
| 2013/0167109 A1* | 6/2013 | Nucci | G06F 9/44 717/105 |
| 2014/0289089 A1* | 9/2014 | Stewart, Jr. | G06Q 10/0631 705/37 |
| 2015/0095358 A1* | 4/2015 | Demo | G06F 16/252 707/758 |
| 2015/0287144 A1* | 10/2015 | Stelman | G06Q 40/12 705/30 |
| 2015/0302382 A1* | 10/2015 | Reicher | G06Q 20/405 705/44 |

OTHER PUBLICATIONS

Naumann et al. Declarative data merging with conflict resolution. In: 7th International Conference on Information Quality, pp. 212-214. 2002. (Year: 2002).*

Tancred Lindholm. XML three-way merge as a reconciliation engine for mobile data. In Proceedings of the 3rd ACM international workshop on Data engineering for wireless and mobile access (MobiDe '03). 2003. (Year: 2003).*

Non-Final Office Action dated Jun. 20, 2019 in U.S. Appl. No. 15/465,911.

Notice of Allowance dated Jul. 12, 2019 in U.S. Appl. No. 15/465,911.

Burns, Lawton R. "The Performance of Group Purchasing Organizations (GPOs) In the Health Care Value Chain: A Literature Review." Retrieved from <https://www.supplychainassociation.org/wp-content/uploads/2018/05/AHA_AH_RM_M_Wharton_2014_LitRe.pdf>. Originally published Sep. 2014. (Year: 2014).

"Contract Manager Setup and User Handbook". SciQuest SelectSite Version Feb. 13, 2013. (Year: 2013).

"Group Purchasing". Health Industry Group Purchasing Association (HIGPA) report. Retrieved from <https://c.ymcdn.com/sites/www.supplychainassociation.org/resource/resmgr/research/gpo_study_business_model.pdf>. Originally published Jul. 2011. (Year:2011).

Improve Sourcing and Contract Management for better Supplier Relationship. Cognizant. Retrieved from <https://www.cognizant.com/services-resources/Services/Improve-Sourcing-and-Contract-Management-White Paper.pdf>. Originally published Feb. 2016. (Year: 2016).

\* cited by examiner

GPOEntityID SERVICE

REQUIRED INFORMATION

702 → ORGANIZATION NAME*
704 → GPOEntityID TYPE*
706 → GPOEntityID VALUE*

OPTIONAL INFORMATION

708 → PHONE TYPE  <SELECT>
EXTERNAL IDENTIFIER TYPE  <SELECT>
710

ADDRESS 1*
ADDRESS 2
ADDRESS 3

PHONE NUMBER  (123)1234-1234
712
EXTERNAL IDENTIFIER VALUE
714

⊘ SINGLE  ≡ BULK
718   720

CITY*
STATE*
COUNTRY*  USA

716

CLEAR   ASSOCIATE

UPDATING CONFLICTING ENTRIES

CROSS REFERENCE TO RELATED APPLICATIONS

This application is a continuation of, claims priority to and the benefit of, U.S. Ser. No. 15/465,911 filed Mar. 22, 2017 and entitled "CONFLICTING NOMENCLATURE RECONCILIATION SYSTEM," which is incorporated by reference in its entirety for all purposes.

FIELD

The present disclosure generally relates to a reconciliation system. More particularly, the disclosure includes a system and method of reconciling data that includes arbitrarily assigned identifiers.

BACKGROUND

Different business entities (e.g., involved in negotiation of a large contract) may use different identifiers and nomenclatures to refer to particular pieces of data. However, referring to an identifier native to a first business entity may result in confusion to a second business entity. Conventional systems do not provide for a reconciliation of these particular pieces of data.

Group purchasing organizations (GPOs) are organizations which negotiate contracts with suppliers on behalf of their members. Members of the GPO are typically healthcare providers and/or distributors. GPOs representing a large number of organizations can generally negotiate contracts with greater power than what a single individual organization could negotiate. For example, an individual healthcare provider may be able to negotiate a five dollar price per box of adhesive bandages, while a GPO could negotiate a three dollar price per box of adhesive bandages, as the GPO purchases in larger quantities.

However, the contracts negotiated by the GPO may be complex. The GPO contract may identify multiple products and multiple healthcare providers. In addition, any one of the multiple healthcare providers may have multiple addresses for various facilities. Further, a given product within the GPO contract may have multiple prices based on the healthcare provider purchasing the product. For example, within the same GPO contract, Hospital A may purchase 1,000 boxes of adhesive bandages at $4 per box, and Clinic C may purchase 50 boxes of adhesive bandages at $4.50 per box. While Clinic C is still able to save by purchasing through the GPO, Clinic C is not able to save as much as Hospital A does, as Hospital A purchases in larger quantities. The various prices may be reflected by a tier ranking system by the GPO.

In order to facilitate the negotiation and execution of such GPO contracts, a contract facilitation system may be used. In an example context, the contracts may be between healthcare providers and suppliers, and the contract may specify a product, a price, and a quantity to be delivered to the healthcare provider at a particular location. All business entities associated with the contracts (e.g., GPOs, healthcare providers, and suppliers) may access a single, central system (or distributed system) where commitments are tracked, using the contract facilitation system. Electronic collaboration among the business entities streamlines the commitment process and tracks history. Optimized price notification between all business entities may be provided in a timely, automated fashion. Thus, the contract facilitation system provides healthcare providers greater visibility into the entire contract process, from proactive notification of new contracts through approval steps and price activation dates.

However, the contract facilitation system is subject to various shortcomings. The contract facilitation system allows GPOs to publish their contracts for suppliers to review before healthcare providers are involved. The larger system also allows GPOs and suppliers to work together to review contracts, agree to eligible participants, and offer terms for delivery to healthcare providers. However, there may be confusion with respect to identifiers used by different entities. GPO contracts are tied to healthcare provider addresses, such as hospital addresses. GPOs may issue GPO-specific identifiers to the healthcare provider addresses, and the GPO-specific identifiers may be arbitrary and not indicative of the provider address. Suppliers may also issue arbitrary supplier-specific account numbers to the healthcare providers and their addresses. From the GPO perspective, a supplier-assigned account number is not sufficient to properly identify a healthcare provider address. Likewise, from the supplier perspective, a GPO-assigned identifier of a hospital address is not sufficient for the supplier to properly identify the healthcare provider address. In short, a GPO's view of information regarding a set of information is not the same as a supplier view of the same information. The healthcare provider itself views the information yet with a different view. Despite this, the contract facilitation system displays the addresses of the healthcare providers as GPO-assigned identifiers, and the suppliers viewing the contracts are unable to readily determine the address of the healthcare provider without performing an extensive and costly manual cross-referencing.

SUMMARY

A method for reconciling conflicting identifiers from a first entity and a second entity is disclosed. The first entity and the second entity may be in a contract for goods to be delivered to an address of an organization. In various embodiments, the method may include receiving, from the first entity via a first user interface, a roster file including an organization identifier and an organization address identifier assigned by the first entity, the organization identifier representing an organization name and the organization address identifier representing the address of the organization. The method may also include updating, in a database, an entry associated with the organization based on the organization identifier and the organization address identifier assigned by the first entity, the entry being associated with the contract between the first entity and the second entity. The method may also include receiving, from the second entity via a second user interface, an account file including an account identifier assigned by the second entity, the account identifier representing the address of the organization. The method may also include updating, in the database, the entry associated with the organization based on the account identifier assigned by the second entity such that the organization address identifier assigned by the first entity is associated with the account identifier assigned by the second entity. The method may also include accessing, by the first user interface, contract details associated with the contract and displaying, on the first user interface, the organization address identifier assigned by the first entity. The method may also include accessing, by the second user interface, the contract details associated with the contract and displaying, on the second user interface, the account identifier assigned by the second entity.

In various embodiments, updating the entry associated with the organization based on the organization identifier and the organization address identifier assigned by the first entity includes searching the database to determine whether the database includes an entry associated with the organization identifier assigned by the first entity, and updating the entry with the organization address identifier assigned by the first entity.

The roster file may further include secondary information associated with the organization. In various embodiments, updating the entry associated with the organization based on the organization identifier and the organization address identifier assigned by the first entity may include searching the database to determine whether the database includes an entry associated with the secondary information associated with the organization, and updating the entry with the organization address identifier assigned by the first entity in response to the secondary information matching a single entry. In various other embodiments, updating the entry associated with the organization based on the organization identifier and the organization address identifier assigned by the first entity may include searching the database to determine whether the database includes searching the database to determine whether the database includes an entry associated with the secondary information associated with the organization, displaying, on the first user interface, a listing of a plurality of entries in response to the secondary information matching more than one entry, receiving, from the first user interface, an identification of a matching entry from the listing of the plurality of entries, and updating the matching entry with the organization address identifier assigned by the first entity. In various other embodiments, updating the entry associated with the organization based on the organization identifier and the organization address identifier assigned by the first entity may include searching the database to determine whether the database includes an entry associated with the secondary information associated with the organization, and creating an entry with the organization address identifier assigned by the first entity in response to the secondary information matching no entries in the database.

In various embodiments, updating the entry associated with the organization based on the organization identifier and the organization address identifier assigned by the first entity may include searching the database to determine whether the database includes an entry associated with the organization address identifier assigned by the first entity, and updating the entry with the organization identifier assigned by the first entity.

In various embodiments, updating the entry associated with the organization based on the organization identifier and the organization address identifier assigned by the first entity may include searching the database to determine whether the database includes an entry associated with the organization address identifier assigned by the first entity, standardizing an address represented by the organization address identifier in response to the database not including an entry associated with the organization address identifier assigned by the first entity, searching the database to determine whether the database includes an entry associated with the standardized address, and updating the entry with the organization location identifier assigned by the first entity in response to the database including the entry associated with the standardized address.

The account file received from the second entity may be a cross-listing file indicating a corresponding organization identifier or organization address identifier for the account identifier. In various embodiments, updating the entry associated with the organization based on the account identifier assigned by the second entity may include searching the database to determine whether the database includes an entry associated with the corresponding organization identifier or organization address identifier, and updating the entry with the account identifier assigned by the second entity in response to the database including the entry associated with the corresponding organization identifier or organization address identifier.

A system for reconciling conflicting identifiers from a first entity and a second entity is also disclosed. The first entity and the second entity may be associated with a contract for goods to be delivered to an address of an organization. In various embodiments, the system may include a database configured to store an entry associated with the organization, the entry including at least one of an organization identifier representing a name of the organization, an organization address identifier representing the address of the organization, or an account identifier representing the address of the organization. The system may also include a first entity user interface configured to receive, from the first entity, a roster file including the organization identifier assigned by the first entity and the organization address identifier assigned by the first entity. The system may also include a second entity user interface configured to receive, from the second entity, an account file including the account identifier assigned by the second entity. The system may also include an entity update unit connected to the first entity user interface and the second entity user interface, the entity update unit configured to update, in the database, the entry associated with the organization based on the received organization identifier assigned by the first entity, the received organization address identifier assigned by the first entity, or the account identifier assigned by the second entity, such that the organization address identifier assigned by the first entity is associated with the account identifier assigned by the second entity. The first user interface may be further configured to access contract details associated with the contract and display the organization address identifier assigned by the first entity. The second user interface may be further configured to access the contract details associated with the contract and display the account identifier assigned by the second entity.

In various embodiments, the system may further include an entity identification unit connected to the entity update unit and configured to search the database to determine whether the database includes an entry associated with the organization identifier assigned by the first entity. In various embodiments, the entity update unit may be configured to update the entry with the organization address identifier assigned by the first entity in response to the database including the entry associated with the organization identifier assigned by the first entity.

The system may further include an entity identification unit connected to the entity update unit and the roster file may further include secondary information associated with the organization. In various embodiments, the entity identification unit may be configured to search the database to determine whether the database includes an entry associated with the secondary information associated with the organization, and the entity update unit is configured to update the entry with the organization address identifier assigned by the first entity in response to the secondary information matching a single entry. In various other embodiments, the entity identification unit is configured to search the database to determine whether the database includes an entry associated with the secondary information associated with the organization, the first user interface is further configured to display a listing of a plurality of entries in response to the secondary information matching more than one entry, and receive an identification, from a user, of a matching entry from the listing of the plurality of entries, and the entity update unit is configured to update the matching entry with the organization address identifier assigned by the first entity. In various other embodiments, the entity identification unit is configured to search the database to determine whether the database includes an entry associated with the secondary information associated with the organization, and the entity update unit is configured to create an entry with the organization address identifier assigned by the first entity in response to the secondary information matching no entries in the database.

In various embodiments, the system further comprises an address identification unit configured to search the database to determine whether the database includes an entry associated with the organization address identifier assigned by the first entity. In these embodiments, the entity update unit updates the entry with the organization identifier assigned by the first entity.

In various embodiments, the system further comprises an address identification unit configured to search the database to determine whether the database includes an entry associated with the organization address identifier assigned by the first entity, standardize an address represented by the organization address identifier in response to the database not including an entry associated with the organization address identifier assigned by the first entity, and search the database to determine whether the database includes an entry associated with the standardized address. In these embodiments, the entity update unit is configured to update the entry with the organization location identifier assigned by the first entity in response to the database including the entry associated with the standardized address.

In various embodiments, the system further comprises an entity identification unit connected to the entity update unit and an address identification unit, and the account file received from the second entity is a cross-listing file indicating a corresponding organization identifier or organization address identifier for the account identifier. In these embodiments, the entity identification unit is configured to search the database to determine whether the database includes an entry associated with the organization identifier assigned by the first entity, the address identification unit is configured to search the database to determine whether the database includes an entry associated with the organization address identifier assigned by the first entity, and the entity update unit is configured to update the entry with the account identifier assigned by the second entity in response to the database including the entry associated with the corresponding organization identifier or organization address identifier.

A method for reconciling conflicting identifiers from a group purchasing organization (GPO) and a supplier is also disclosed. The GPO and the supplier are with a contract for goods to be delivered to an address of a healthcare provider. In various embodiments, the method may include receiving, from the GPO via a GPO user interface, a roster file including a GPO-assigned healthcare provider identifier representing a name of the healthcare provider and a GPO-assigned healthcare provider address identifier representing an address of the healthcare provider. In various embodiments, the method includes updating, in a database, an entry associated with the healthcare provider and the contract based on the GPO-assigned healthcare provider identifier and the GPO-assigned healthcare provider address identifier.

In various embodiments, the method includes receiving, from the supplier via a supplier user interface, an account file including a supplier-assigned account identifier representing the address of the healthcare provider. In various embodiments, the method includes updating, in the database, the entry associated with the healthcare provider based on the supplier-assigned account identifier such that the GPO-assigned healthcare provider address identifier is associated with the supplier-assigned account identifier. In various embodiments, the method includes accessing, by the GPO user interface, contract details associated with the contract and displaying, on the GPO user interface, the GPO-assigned healthcare provider address identifier. In various embodiments, the method includes accessing, by the supplier user interface, the contract details associated with the contract and displaying, on the supplier user interface, the supplier-assigned account identifier.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

A more complete understanding of the present disclosure may best be obtained by referring to the detailed description and claims when considered in connection with the figures, wherein like numerals denote like elements.

FIG. 7 illustrates an exemplary user interface, in accordance with various embodiments.

DETAILED DESCRIPTION

Figure 1:
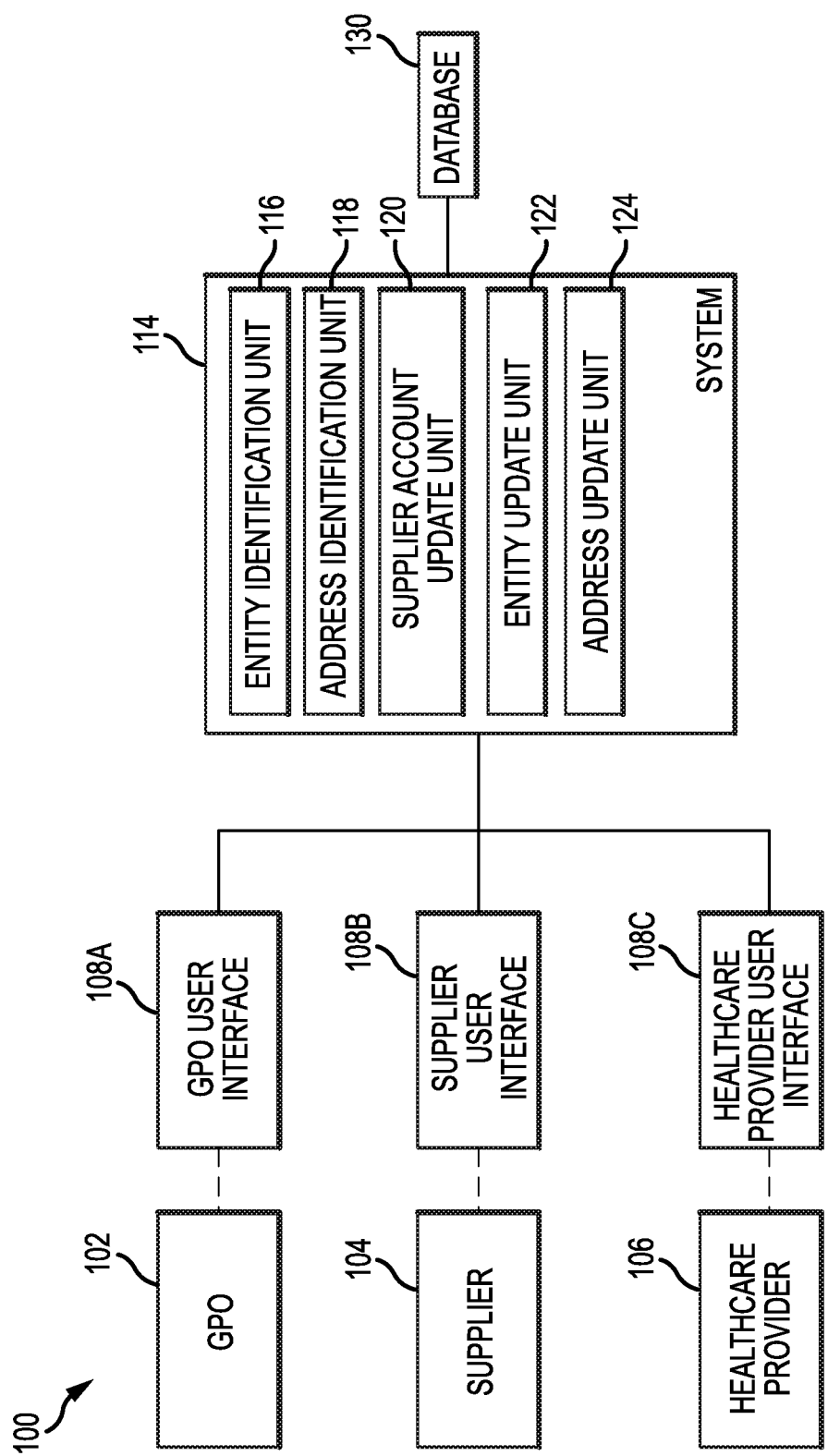
FIG. 1 illustrates a block diagram of the conflicting nomenclature reconciliation system, in accordance with various embodiments.

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented. Furthermore, any reference to singular may include plural embodiments, and any reference to more than one component or step may include a singular embodiment or step. It is to be understood that reference to an item in the singular may also include the item in the plural, and plural may include singular. All ranges and ratio limits disclosed herein may be combined.

The present disclosure is described in one or more embodiments in the following description with reference to the figures, in which like numerals represent the same or similar elements. While the disclosure is described in terms of the best mode for achieving the disclosure's objectives, it will be appreciated by those skilled in the art that it is intended to cover alternatives, modifications, and equivalents as may be included within the spirit and scope of the disclosure as defined by the appended claims and their equivalents as supported by the following disclosure and drawings.

The conflicting nomenclature reconciliation system may be part of the larger contract facilitation system which allows suppliers and GPOs to establish contracts. The conflicting nomenclature reconciliation system enables the various entities to view information which was previously author-specific, in terms established by the viewing entity. This obstacle exists, in part because the healthcare industry has a particular, long-felt need for harmonization of identifiers, as there is no universally recognized and implemented identification system for healthcare provider locations.

The conflicting nomenclature reconciliation system described herein uses loosely structured information (or separately managed information) from a GPO and determines the best healthcare provider match based on at least one of address, organization attributes (e.g., organization name, organization identification numbers, phone numbers, etc.), product, profile, and network strength to best match the GPO contracts to the appropriate healthcare provider address. As described herein, the system not only matches the healthcare provider name, but also matches the healthcare provider address, as ultimately the contracts are fulfilled by the supplier sending the goods to the appropriate healthcare provider address.

FIG. 1 illustrates a block diagram of the contract facilitation system 100. The contract facilitation system 100 includes GPO 102, supplier 104, healthcare provider 106, GPO user interface 108A, supplier user interface 108B, healthcare provider user interface 108C, the conflicting nomenclature reconciliation system 114, which includes an entity identification unit 116, an address identification unit 118, a supplier account update unit 120, an entity update unit 122, and an address update unit 124, and a database 130. A GPO 102 may interact with the conflicting nomenclature reconciliation system 114 via a GPO user interface 108A. The GPO user interface 108A may be a display and a computing device used by the GPO 102 to access the conflicting nomenclature reconciliation system 114. The GPO user interface 108A may be a software interface provided by the conflicting nomenclature reconciliation system 114 for communicating with the GPO 102. As used herein, GPO may refer to the entire GPO or one or more individuals representing the GPO. While FIG. 1 illustrates the conflicting nomenclature reconciliation system 114 being separate from the user interfaces 108 and the database 130, they may be included within the conflicting nomenclature reconciliation system 114 in various embodiments. That is, in a first embodiment, the conflicting nomenclature reconciliation system 114 includes the user interfaces 108 but not the database 130. In a second embodiment, the conflicting nomenclature reconciliation system 114 does not include the user interfaces 108 but includes the database 130. In a third embodiment, the conflicting nomenclature reconciliation system 114 includes both the user interfaces 108 and the database 130.

A supplier 104 may interact with the conflicting nomenclature reconciliation system 114 via a supplier user interface 108B. The supplier user interface 108B may be a display and a computing device used by the supplier 104 to access the conflicting nomenclature reconciliation system 114. The supplier user interface 108B may be a software interface provided by the system 114 for communicating with the supplier 104. As used herein, supplier may refer to the entire supplier organization or one or more individuals representing the supplier.

A healthcare provider 106 may interact with the conflicting nomenclature reconciliation system 114 via a healthcare provider user interface 108C. The healthcare provider user interface 108C may be a display and a computing device used by the healthcare provider 106 to access the conflicting nomenclature reconciliation system 114. The healthcare provider user interface 112 may be a software interface provided by the conflicting nomenclature reconciliation system 114 for communicating with the healthcare provider 106. As used herein, healthcare provider may refer to the entire healthcare provider organization or one or more individuals representing the healthcare provider. Also as used herein, healthcare provider may refer to an organization (e.g., ExampleHealthcareGroup) as well as facilities associated with the organization (e.g., ExampleHealthcare Pediatric Center) and healthcare professionals working for the organization (e.g., doctors, nurses, physician's assistants).

The various units 116-124 within the conflicting nomenclature reconciliation system 114 allow the GPO 102, the supplier 104, or the healthcare provider 106 to view information in their respective terms, via their respective user interfaces 108. The database 130 stores the data used by the GPO 102, supplier 104, and the healthcare provider 106 in establishing a GPO contract. The database 130 is configured to serve as a master data information repository.

Figure 2:
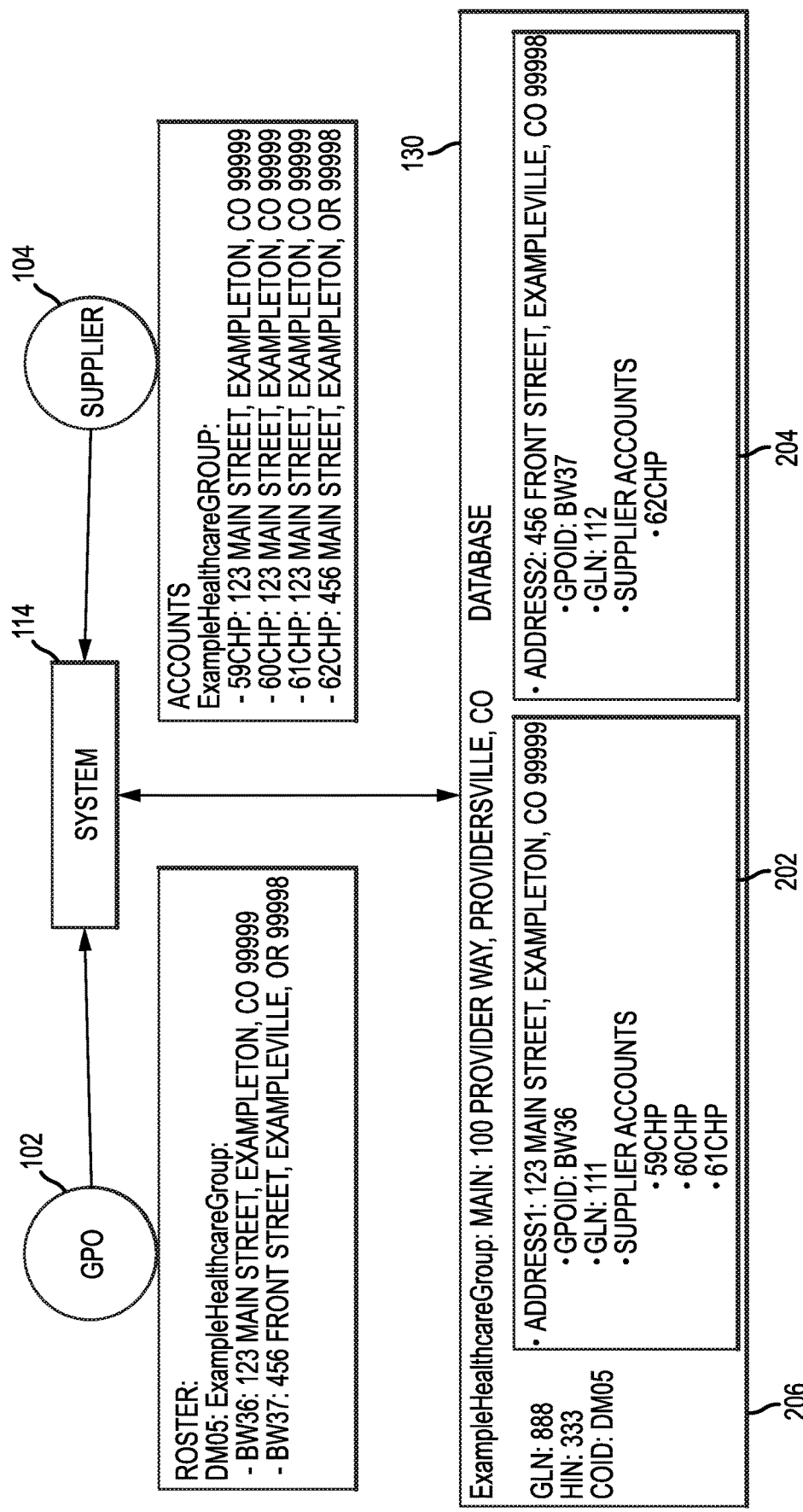
FIG. 2 illustrates an example of data structures used in the conflicting nomenclature reconciliation system, in accordance with various embodiments.

FIG. 2 illustrates an example embodiment of the different identifiers and data structures used by the various business entities. In an example embodiment, MegaGPO is a GPO 102, SupplierTech is a supplier 104, and ExampleHealthcareGroup is a healthcare provider 106.

Each GPO (e.g., MegaGPO) maintains a roster of healthcare providers and healthcare provider addresses, each identified with a GPO-assigned identifier. The GPO-assigned healthcare provider identifier represents the healthcare provider, such as ExampleHealthcareGroup. The GPO-assigned healthcare provider address identifier represents a healthcare provider address of the healthcare provider or healthcare provider facility, such as 123 Main Street, Exampleton, CO 99999. The GPO-assigned healthcare provider identifier and/or the GPO-assigned healthcare provider address identifier may be a number, a string of letters, or a combination of numbers, letters, and symbols. For example, the GPO-assigned healthcare provider identification for ExampleHealthcareGroup may be DM05, and the GPO-assigned healthcare provider address identifier for 123 Main Street, Exampleton, CO 99999 may be BW36.

A healthcare provider may have multiple locations or facilities, each with unique GPO-assigned healthcare provider address identifiers. For example, ExampleHealthcareGroup may also have a location at 456 Front Street, Exampleville, OR 99998, which corresponds to GPO-assigned healthcare provider address identifier BW37. As shown in the examples, the GPO-assigned healthcare provider identifier and/or the GPO-assigned healthcare provider address identifier may be arbitrary and an individual reading the GPO-assigned identifiers may not be able to discern that BW36 corresponds to 123 Main Street, Exampleton, CO 99999. In addition, the location may be an address of a facility or a location of a room or area within the facility (e.g., operating room 7B or pharmacy storage room).

Each supplier (e.g., SupplierTech) maintains a list of accounts. As shown in FIG. 2, SupplierTech's account list includes ExampleHealthcareGroup and multiple supplier-assigned account identifiers (e.g., 59CHP, 60CHP, 61CHP, 62CHP) may be associated with ExampleHealthcareGroup. The multiple supplier-assigned account identifiers may be associated with various healthcare provider locations.

In addition, more than one supplier-assigned account identifier may be associated with a single location. As shown in FIG. 2, 59CHP, 60CHP, and 61CHP are associated with ExampleHealthcareGroup located at 123 Main Street, Exampleton, CO 99999 and 62CHP is associated with ExampleHealthcareGroup located at 456 Front Street, Exampleville, OR 99998.

The conflicting nomenclature reconciliation system 114 may receive a roster file from the GPO. The roster file may include the GPO-assigned identifiers and their corresponding data (e.g., names and addresses of healthcare providers). Likewise, the supplier 104 may provide to the system 114 an account list identifying its supplier-assigned account identifiers and their corresponding data (e.g., names and addresses of healthcare providers).

Alternatively, or in addition, if known, the supplier may provide a table or spreadsheet which cross-references GPO-assigned identifiers (e.g., GPO-assigned healthcare provider identifiers and/or the GPO-assigned healthcare provider address identifiers) with supplier-assigned account identifiers corresponding to the respective healthcare provider and healthcare provider address. In the example shown in FIG. 2, the supplier-assigned account identifier of 59CHP, 60CHP, and 61CHP corresponds to ExampleHealthcareGroup located at 123 Main Street, Exampleton, CO 99999, which corresponds to GPO-assigned healthcare provider identifier DM05 and the GPO-assigned healthcare provider address identifier BW36. Accordingly, supplier-assigned account identifier 62CHP corresponds to GPO-assigned healthcare provider identifier DM05 and the GPO-assigned healthcare provider address identifier BW37.

The database 130 receives the data from the GPO and/or the supplier and stores the data. As shown in FIG. 2, database 130 includes data associated with ExampleHealthcareGroup in a healthcare provider data structure 206. The healthcare provider data structure 206 may be associated with a system-assigned identifier. The system-assigned identifier may be different from the GPO-assigned and supplier-assigned identifiers and may only be recognizable to the conflicting nomenclature reconciliation system 114.

The healthcare provider data structure 206 includes information from the roster data provided by GPO 102 and the account data provided by supplier 104. The healthcare provider data structure 206 includes the GPO-assigned healthcare provider identifier DM05. The healthcare provider data structure 206 may have a first entry 202 within the healthcare provider data structure 206 for a first location at 123 Main Street, Exampleton, CO 99999. The first entry 202 may also include GPO-assigned healthcare provider address identifier BW36 and supplier-assigned account identifiers 59CHP, 60CHP, and 61CHP associated with the first location at 123 Main Street, Exampleton, CO 99999. The healthcare provider data structure 206 may also have a second entry 204 within the healthcare provider data structure 206 for a second location at 456 Front Street, Exampleville, OR 99998. The second entry 204 may also include GPO-assigned healthcare provider address identifier BW37 and supplier-assigned account identifier 62CHP.

In addition to the data from the GPO and the supplier, the healthcare provider data structure 206 includes additional information. The additional information may include a main address of the healthcare provider and various third-party assigned identifiers, such as a Global Location Number (GLN), a Health Industry Number (HIN), a Drug Enforcement Administration (DEA) identifier, Data Universal Numbering System (DUNS) identifier, or Federal Employer Identification Number (FEIN). As shown in FIG. 2, the main address is 100 Provider Way, Providersville, CO, a GLN of the healthcare provider is 888, a HIN of the healthcare provider is 333, a GLN of the first location of the healthcare provider is 111, and a GLN of the second location of the healthcare provider is 112. These additional pieces of information may be obtained from various sources, such as purchase orders processed by the contract facilitation system, website listings associated with each healthcare provider and healthcare provider location, manual entry of information from the GPO, supplier, or healthcare provider, or any other manner in which data may be accumulated over time. In response to the identifier being issued and maintained by a third party, such as DUNS, the identifier may be validated before it is used as search criteria.

Figure 3A:
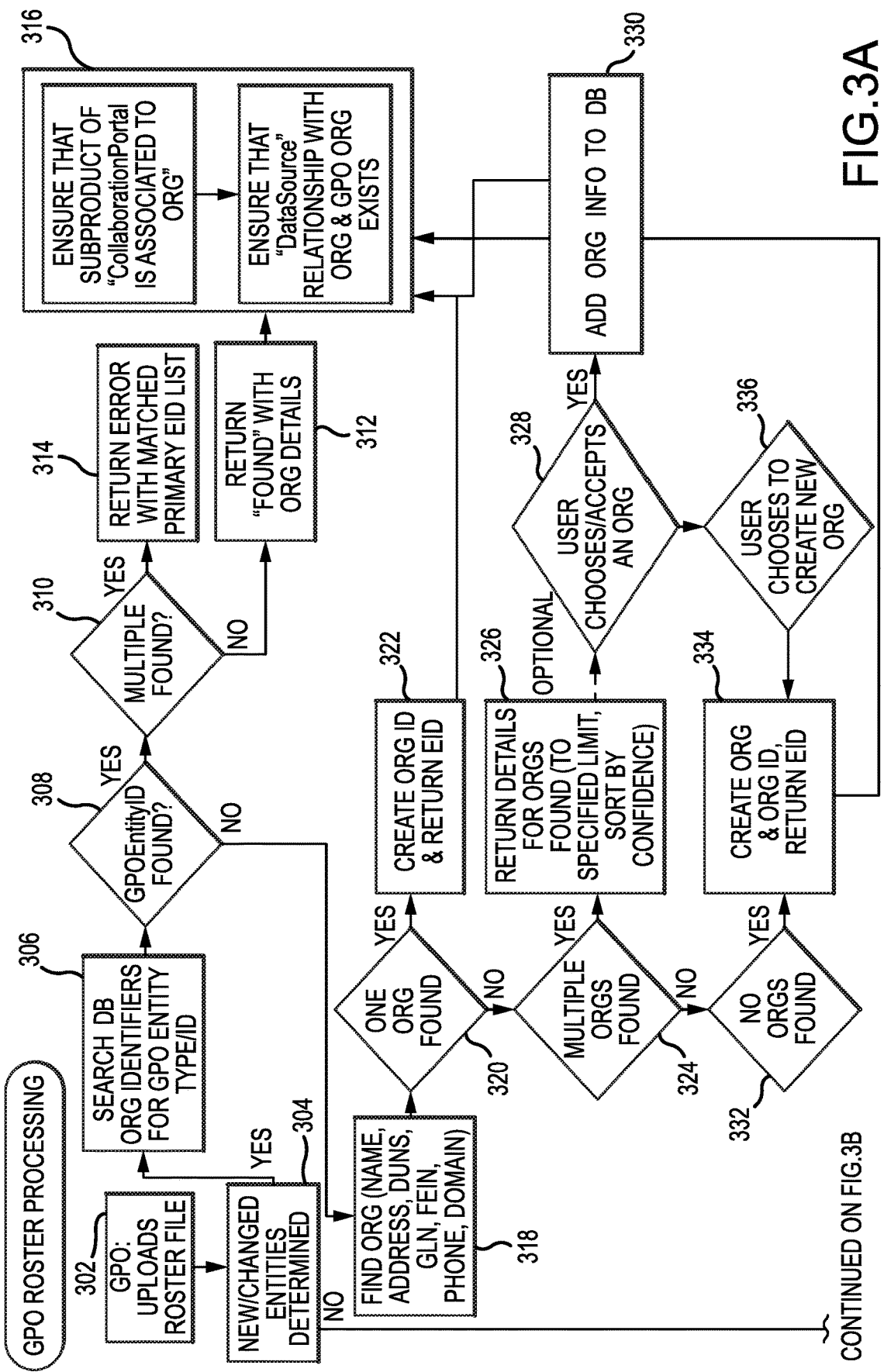
FIG. 3A is a first part of a flowchart illustrating processing of roster data provided by a GPO, in accordance with various embodiments.
Figure 3B:
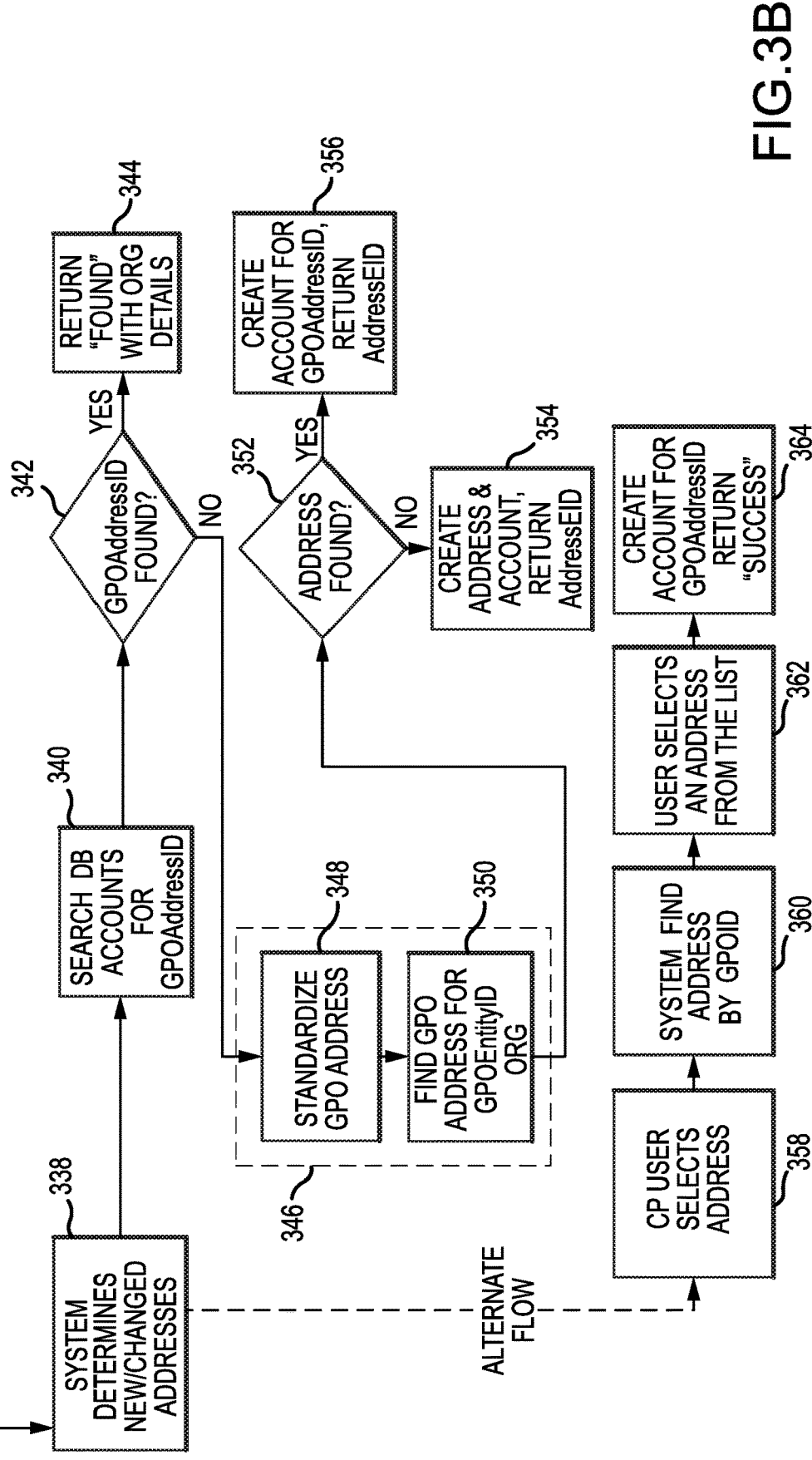
FIG. 3B is a second part of a flowchart illustrating processing of roster data provided by a GPO, in accordance with various embodiments.

As described herein, the GPO may provide a roster to the conflicting nomenclature reconciliation system 114 to supplement the database 130. FIGS. 3A and 3B illustrate a process of importing the roster data from the GPO 102 to the database 130. The GPO 102 uploads the roster file to the system 114 (step 302). The GPO 102 may upload the roster file to the system 114 via the GPO user interface 108A. Whether there are new or changed entities in response to comparing the uploaded roster file to the database 130 is determined (step 304). In some embodiments, the entity update unit 122 determines whether there are new or changed entities by comparing the uploaded roster file to the database 130.

In response to the conflicting nomenclature reconciliation system 114 determining there are new or changed entities, for each entity (e.g., healthcare provider) in the uploaded roster file, the database 130 is searched for a matching healthcare provider (step 306). The entity identification unit 116 may search the database 130. The database 130 may be searched by GPO-assigned healthcare provider identifiers. In response to a matching healthcare provider being found based on GPO-assigned healthcare provider identifier (step 308), whether multiple matching healthcare providers are found is determined (step 310). In response to multiple matching healthcare providers being found, an error is returned with a list of matching healthcare providers (step 314). That is, in response to multiple GPO-assigned healthcare provider identifiers within the database 130 matching a particular healthcare provider identifier from the uploaded roster file, an error is returned, as GPO-assigned healthcare provider identifiers should be unique. The user may identify which of the multiple healthcare providers corresponds to the particular healthcare provider from the uploaded roster file.

In response to only a single healthcare provider being found in the database 130 based on GPO-assigned healthcare provider identifier from the uploaded roster file, the healthcare provider details are accessed from the database 130 and presented via the GPO user interface 108 (step 312). The details of the matched healthcare provider are verified with the uploaded roster file (step 316). Any additional details from the uploaded roster file associated with the matched healthcare provider that are not already in the database 130 may be added to the database 130. The entity update unit 122 may update the database 130 with the GPO-assigned healthcare provider address identifier, if not already in the database 130.

Referring back to step 308, in response to no healthcare provider from the database 130 matching the GPO-assigned healthcare provider identifier of the particular healthcare provider from the uploaded roster file, the database 130 is searched based on other healthcare provider information, such as name of the healthcare provider, address of the healthcare provider, DUNS, GLN, FEIN, phone number, or internet domain (step 318). The entity identification unit 116 may search the database 130. In response to a single healthcare provider being found from the database 130 that matches the particular healthcare provider from the uploaded roster file based on the other healthcare provider information (step 320), the GPO-assigned healthcare provider identifier from the roster file associated with the healthcare provider is added to the healthcare provider entry in the database 130 (step 322). The entity update unit 122 may add the GPO-assigned healthcare provider identifier and/or the GPO-assigned healthcare provider address identifier to the corresponding entry in the database 130.

In response to multiple healthcare providers being matched based on the other healthcare provider information (step 324), the multiple healthcare providers may be ranked and presented to the GPO 102 via the GPO user interface 108 (step 326). The multiple healthcare providers may be ranked based on any number of criteria, including confidence level, as described herein. The GPO 102 may identify a healthcare provider from the list of multiple healthcare providers presented on the GPO user interface 108 (step 328) and the information associated with the selected healthcare provider from the uploaded roster file is updated in the database 130 (step 330). Alternatively, instead of presenting the multiple matched healthcare providers to the GPO 102 and receiving a selection from the GPO 102, a most likely match may be automatically determined by the system and the organization information for that automatically determined match is added to the database 130. The criteria for automatic determination may be any criteria described herein, including confidence level.

The entity update unit 122 may update the database 130. The GPO 102 may choose to not identify a healthcare provider from the list of multiple healthcare providers (step 336) and instead create a new healthcare provider entry in the database 130 (step 334). The new healthcare provider entry may be created by the entity update unit 122.

In response to no healthcare providers being matched based on the other healthcare provider information (step 332), a new healthcare provider entry is created in the database 130 (step 334). Again, the new healthcare provider entry may be created by the entity update unit 122.

FIG. 3B continues the process shown in FIG. 3A. In response to no new or changed entities being in the uploaded roster file, the system 114 determines whether there are any new or changed addresses (step 338). The address identification unit 118 may determine whether there are any new or changed addresses. In response to no new or changed addresses existing, the process ends. In response to new or changed addresses, for each new or changed address, the database 130 is searched for GPO-assigned healthcare provider address identifiers (step 340). The address identification unit 118 may search the database 130 for the GPO-assigned healthcare provider address identifiers. In response to a GPO-assigned healthcare provider address identifier being matched, the healthcare provider details are presented to the GPO via the GPO user interface 108 (step 344).

In response to no GPO-assigned healthcare provider address identifiers being matched, the actual address is searched for in the database 130 (step 346). Again, the address identification unit 118 may search for the actual address in the database. Within the step of searching for the actual address in the database 130, the address provided in the uploaded roster file may be standardized to meet a uniform format, such as a format specified by the USPS (step 348). A third party standardization service may be used.

The standardized address is then searched for in the database 130 (step 350). Whether the address is found in the database 130 is determined (step 352). In response to the address being found, an address identifier is created (step 356). The address update unit 124 may create the address identifier. Similar to the healthcare provider identifier, the GPO-assigned healthcare provider address identifier may serve as the address identifier, but in response to the GPO-assigned healthcare provider location being undetermined, a system-assigned address identifier recognizable to the database 130 is created.

In response to the address not being found, a new entry is created in the database 130 (step 354). The entity update unit 124 may create the new entry in the database 130. The new entry may include associated data from the roster file. In response to additional information being provided to the database 130, the new entry may later be merged with another healthcare provider entry or supplemented with the additional information. Eventually, the GPO-assigned healthcare provider address identifier may match with a supplier-assigned account identifier.

Alternatively, in response to a new or changed address in the roster file, the GPO 102 may select an address from the roster file (step 358) and the system 114 may search the database 130 for addresses matching the GPO-assigned healthcare provider identifier associated with the selected address from the roster file (step 360). More specifically, the address identification unit 118 may search the database 130 for the address matching the GPO-assigned healthcare provider identifier. There may be one or more matching addresses in the database 130 which correspond to the GPO-assigned healthcare provider identifier, and the GPO 102 selects an address from the one or more matching addresses (step 362) and a new entry is created, as described herein (step 364).

Figure 4:
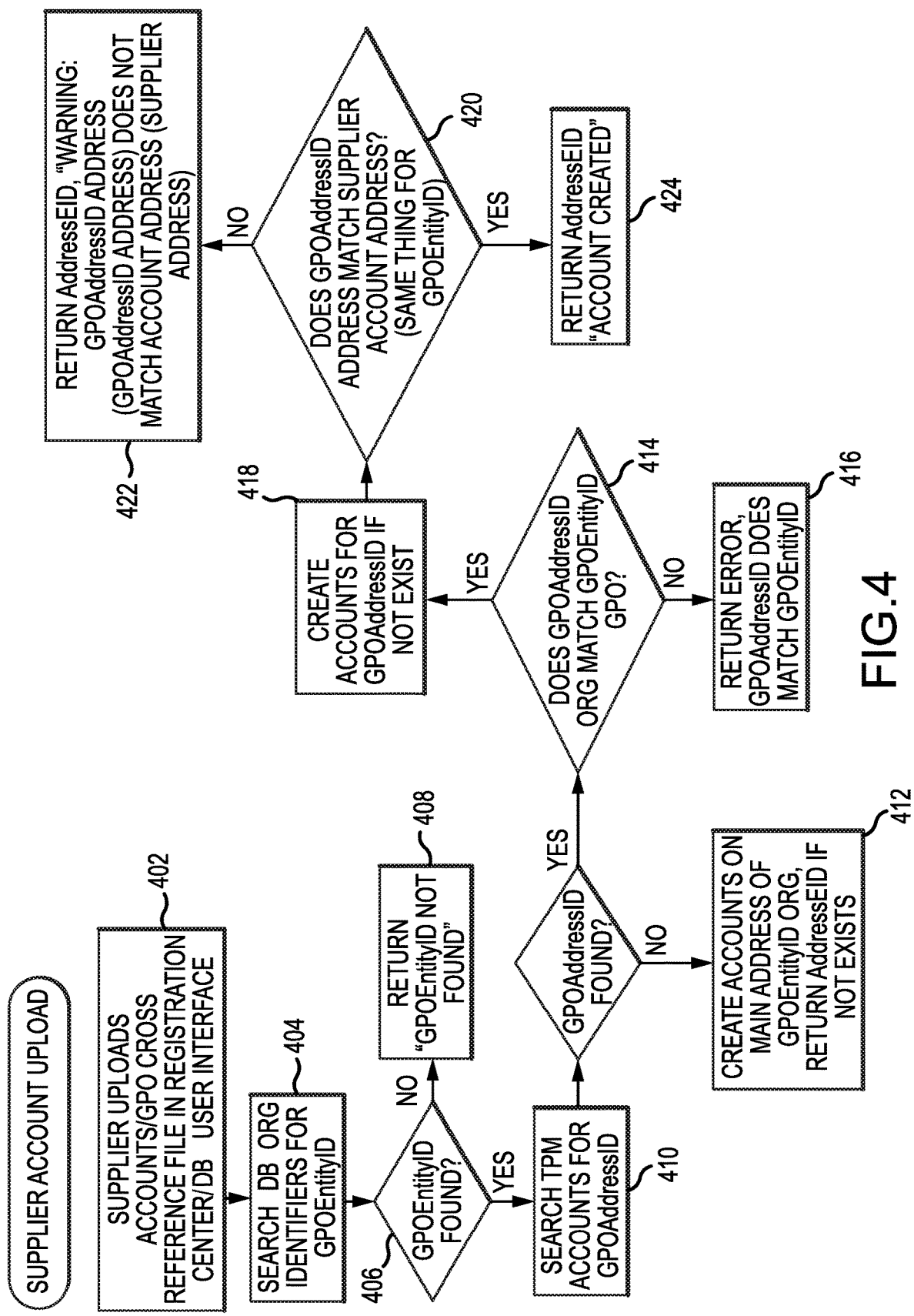
FIG. 4 is a flowchart illustrating processing of account data provided by a supplier, in accordance with various embodiments.

FIG. 4 illustrates a process for a supplier to upload a list of accounts, according to an embodiment of the invention.

The supplier 104 may upload a cross-listing of supplier-assigned account identifiers and GPO-assigned healthcare provider identifiers and/or GPO-assigned healthcare provider address identifiers (step 402). This upload may be performed in response to the supplier 104 registering with the contract facilitation system. This upload may be facilitated using the supplier user interface 108B. The cross-listing may be a table, an array, a spreadsheet, or any other data structure having at least two paired data points.

The database 130 is searched for stored identifiers matching the GPO-assigned healthcare provider identifiers in the cross-listing (step 404). The entity identification unit 116 may perform this search. For each GPO-assigned healthcare provider identifier in the cross-listing, it is determined whether the GPO-assigned healthcare provider identifier is in the database 130 (step 406). In response to the GPO-assigned healthcare provider identifier not being in the database 130, an indication that the particular GPO-assigned healthcare provider identifier is not in the database 130 is displayed on the supplier user interface 110 (step 408).

In response to the GPO-assigned healthcare provider identifier being in the database 130, the database 130 is searched for stored identifiers matching the GPO-assigned healthcare provider address identifiers in the cross-listing associated with the matched GPO-assigned healthcare provider identifier (step 410). The address identification unit 118 may perform this search. In response to the GPO-assigned healthcare provider address identifier not being found in the database 130, an entry is created in the database 130 associating the GPO-assigned healthcare provider identifier and the GPO-assigned healthcare provider address identifier with the supplier-assigned account identifier specified in the cross-listing (step 412). The entity update unit 122 may create the entry in the database 130.

In response to the GPO-assigned healthcare provider address identifier being found in the database 130, whether the matched GPO-assigned healthcare provider identifier is associated with the GPO-assigned healthcare provider address identifier in the database 130 is determined (step 414). In response to not being associated, an error is returned on the supplier user interface 108B, as there may be an error in the cross-listing (step 416). In response to being associated, an entry is created in the database 130 associating the GPO-assigned healthcare provider identifier and the GPO-assigned healthcare provider address identifier with the supplier-assigned account identifier specified in the cross-listing (step 418).

Whether the address in the database 130 associated with the GPO-assigned healthcare provider address identifier matches the address in the database 130 associated with the supplier-assigned account identifier is determined (step 420). The address identification unit 118 may perform step 420. In addition, whether the name associated with the GPO-assigned healthcare provider identifier matches the name in the database 130 associated with the supplier-assigned account identifier may be determined. The entity identification unit 116 may make this determination. In response to the addresses and/or the names not matching, an error is returned to the supplier 104 via the supplier user interface 108B (step 422). In response to the addresses and/or the names matching, an entry is created in the database 130 associating the supplier-assigned account identifier with the GPO-assigned healthcare provider identifier and the GPO-assigned healthcare provider address identifier (step 424). In various embodiments, step 420 may not be performed, and after the entry is created in step 418, a notification is displayed indicating that the entry was created.

Figure 5:
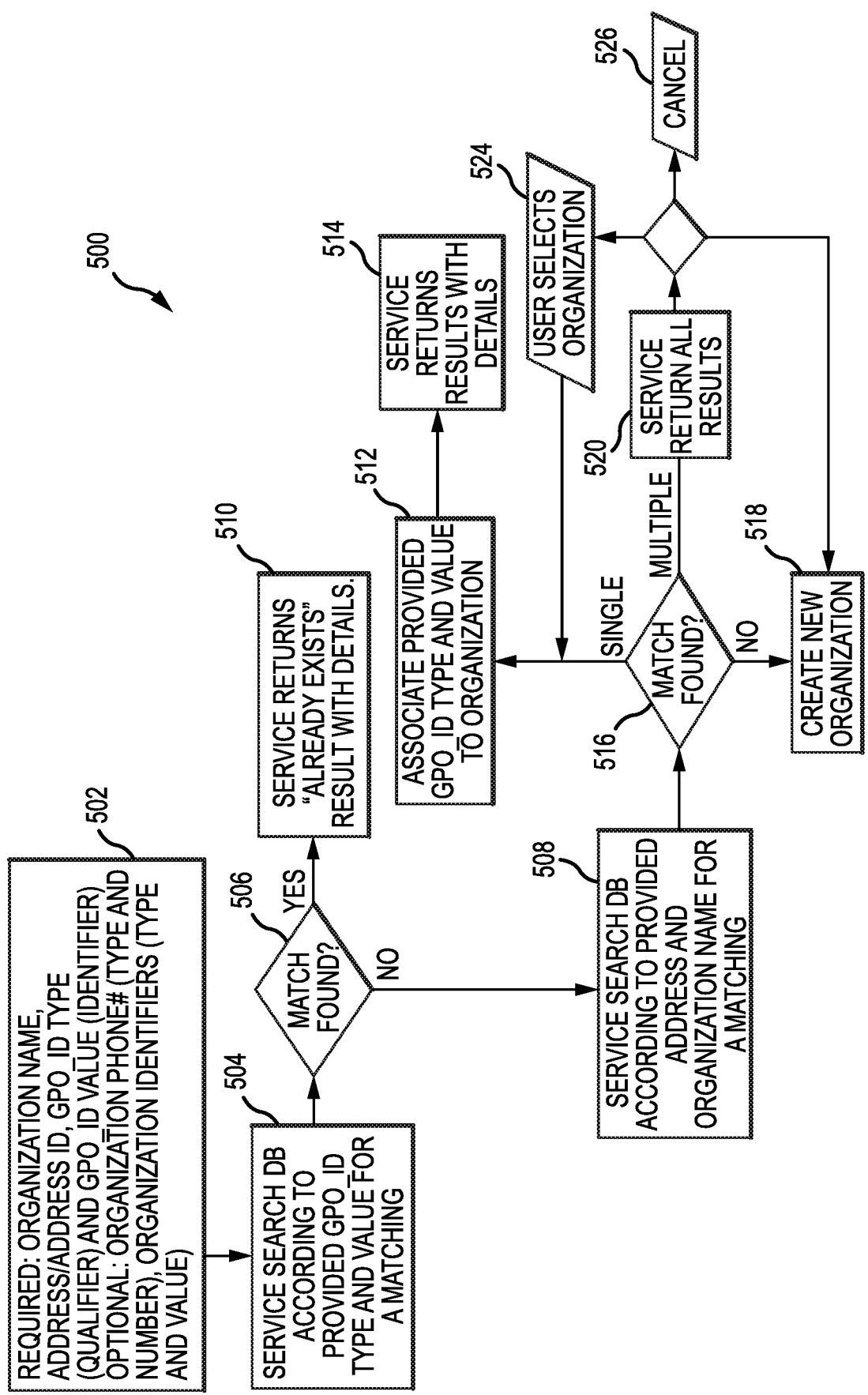
FIG. 5 is a flowchart illustrating association of a GPO-assigned identifier with an entry in the database, in accordance with various embodiments.

FIG. 5 illustrates a process 500 of associating a GPO-assigned healthcare provider identifier with a healthcare provider entry in the database 130. The process 500 may be used in response to the healthcare provider entry in the database 130 not having an associated GPO-assigned healthcare provider identifier. Process 500 may be initiated by a user, as described below, or may be used in a different process (e.g., process 300).

The entity identification unit 116 receives, from a user interface (e.g., GPO user interface 108A, supplier user interface 108B, or healthcare provider user interface 108C), at least one of a healthcare provider name, a healthcare provider address, an entity identifier type (e.g., GPO-assigned healthcare provider identifier or GPO-assigned healthcare provider address identifier), an entity identifier (e.g., BW36, 61CHP, or DM05), or a system-assigned electronic identification (EID) of the healthcare provider. The entity identification unit 116 may also receive, from the user interface, other information for searching for a particular healthcare provider within the database 130, such as a phone number, a phone number type, or third party identification numbers, such as GLN, HIN, DEA identifier, or DUNS identifier (step 502).

The entity identification unit 116 searches the database 130 based on the one or more pieces of data received from the user interface 108 (step 504). Whether a match is found based on the GPO-assigned healthcare provider identifier is determined (step 506). In response to a match being found based on the GPO-assigned healthcare provider identifier, the entity identification unit 116 instructs the user interface 108 to display the matched healthcare provider, including the system-assigned identification number and details associated with the matched healthcare provider (step 510).

In response to a match not being found based on the GPO-assigned healthcare provider identifier, the entity identification unit 116 searches the database 130 based on the other information (step 508) and whether one or more matches are found is determined (step 510).

In response to a single match being found based on the data provided other than the GPO-assigned healthcare provider identifier, the provided GPO-assigned healthcare provider identifier is assigned with the matched entry from the database 130 (step 512) and all of the healthcare provider details are displayed on the user interface 108 (step 514). In addition, in response to a match being found based on a subset of the provided one or more pieces of data, the remaining provided data may be used to supplement the entry associated with the healthcare provider in the database 130. For example, if a GPO-assigned healthcare provider identifier, an address, a name, and a phone number were provided to the entity identification unit 116 via the user interface 108, and the entity identification unit 116 matched a healthcare provider entry in the database based on address and phone number, the entry may be supplemented with the GPO-assigned healthcare provider identifier and name. In this way, the new piece of data (the GPO-assigned healthcare provider identifier and name) supplements the database 130.

In response to multiple matches being found, the multiple matches may be shown (step 520). The multiple matches may be sorted by confidence level. In some embodiments, confidence level may be determined based on the services the potential match uses, or an activity level of the potential match. For example, a query for a healthcare provider name including "Wellness Care," located in California, and having a GPO-assigned healthcare provider identifier of 481516 and a GPO-assigned healthcare provider address identifier of 2342 may be input into a user interface 108. The entity identification unit 116 may not be able to find a matching entry in the database 130 for the GPO-assigned healthcare provider identifier or the GPO-assigned healthcare provider address identifier. However, 25 results matching "Wellness Care" in California may be found in the database 130. The 25 results may be sorted by activity level, such as number of contracts with GPOs established or number of contracts with GPOs established within the last 6 months.

The proper healthcare provider from the results may be identified using the user interface 108 (step 524), the database 130 may be updated (step 512), and all of the healthcare provider details are displayed on the user interface 108 (step 514).

If no entry from the results is the corresponding healthcare provider, a new entry may be created in the database 130 (step 518). Alternatively, the entire process may be cancelled (step 526).

In addition, if no matches are found, a new entry may be created in the database 130 (step 518). However, a status indicator of how reliable the information is may be set to a low value. The reliability status indicator may be increased as more information is added to the entry from different sources.

Address identification unit 118 receives, from a user interface (e.g., GPO user interface 108A, supplier user interface 108B, or healthcare provider user interface 108C), at least one of a system-assigned electronic identification (EID) of the healthcare provider, a healthcare provider address, an entity identifier type (e.g., GPO-assigned healthcare provider identifier or GPO-assigned healthcare provider address identifier), an entity identifier (e.g., BW36, 61CHP, or DM05), or a system-assigned identifier of a GPO. The entity identification unit 116 may also receive, from the user interface, other information for searching for a particular address within the database 130, such as an address type (e.g., hospital, pharmacy).

The address identification unit 118 searches the database 130 for an entry based on the provided data from the user interface 108. In response to an address being used to search the database 130, the address received from the user interface 108 may be normalized using the processes described herein, such that a consistent format is used for the address search.

In response to an entry being matched based on the search, the database 130 is supplemented with information provided by the user interface 108 which was not already present in the database 130. In response to an entry not being matched, then an entry is created with the information provided by the user interface 108.

Figure 6:
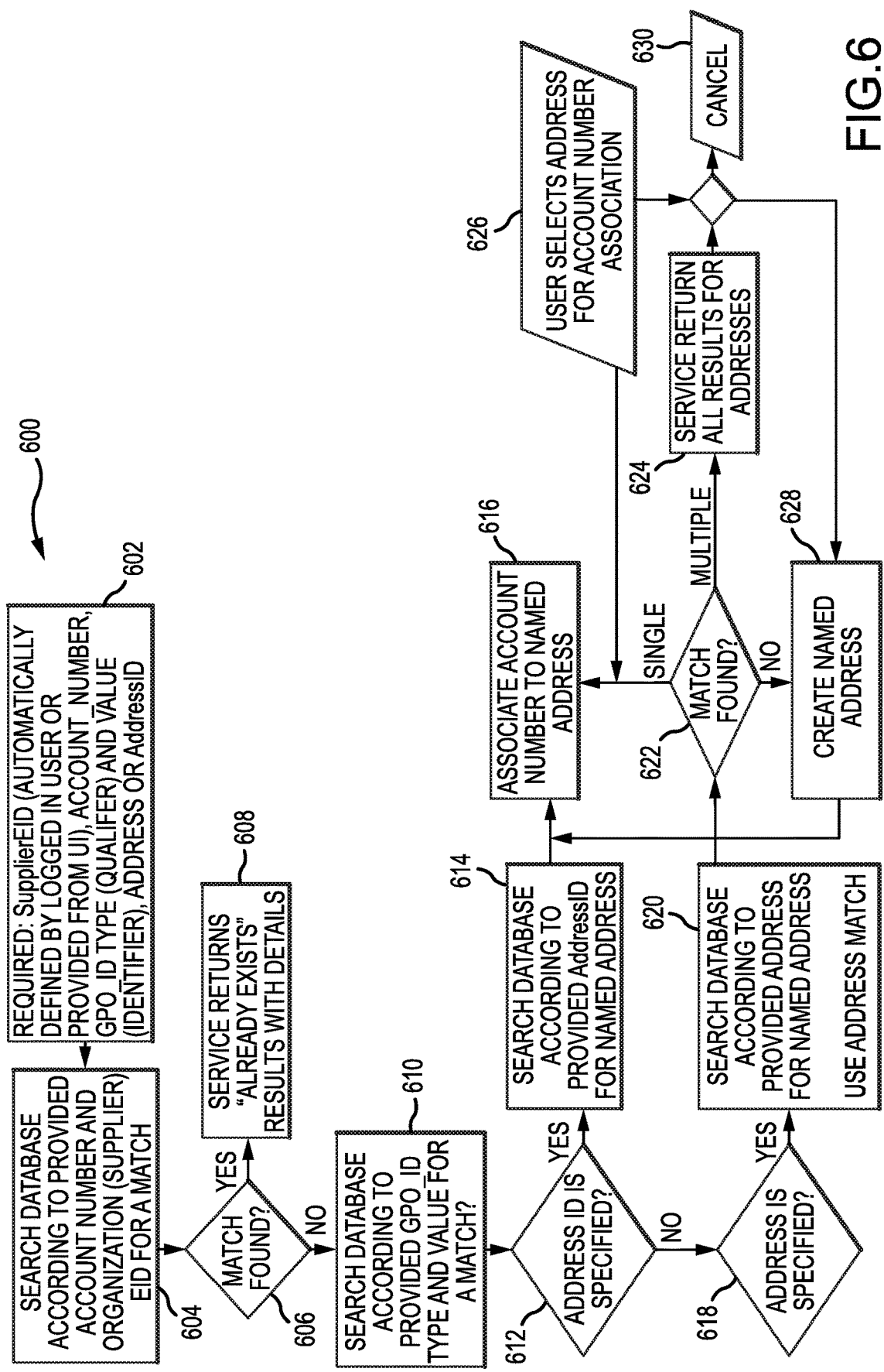
FIG. 6 is a flowchart illustrating association of a supplier-assigned account identifier with an entry in the database, in accordance with various embodiments.

FIG. 6 illustrates a process 600 for associating a supplier-assigned account identifier with an entry in the database, in accordance with various embodiments.

The supplier account update unit 120 receives, from a supplier 104 via the supplier user interface 108B, at least one of a system-assigned identifier, a list of supplier-assigned account identifiers associated with a particular healthcare provider location, a GPO-assigned healthcare provider identifier, a GPO-assigned healthcare provider address identifier associated with the particular healthcare provider, an address of the healthcare provider, and a remove-by-omission flag (step 602).

For each supplier-assigned account identifier in the list of supplier-assigned account identifiers, the supplier account update unit 120 searches the database 130 for a particular healthcare provider based on the provided supplier-assigned account identifier and GPO-assigned healthcare provider identifier (step 604). Whether a match is found based on the provided supplier-assigned account identifier and GPO-assigned healthcare provider identifier is determined (step 606). In response to a match being found, an indication that the association between supplier-assigned account identifier and the GPO-assigned healthcare provider identifier already exists is displayed on the user interface 108.

In response to a match not being found, the supplier account update unit 120 searches the database 130 based on the other information provided (step 610). In response to a GPO-assigned healthcare provider address identifier being provided (step 612), the database 130 is searched for the GPO-assigned healthcare provider address identifier (step 614). In response to the GPO-assigned healthcare provider address identifier being matched, the supplier-assigned account identifier is associated with the entry in the database corresponding with the matched GPO-assigned healthcare provider address identifier (step 616).

In response to no GPO-assigned healthcare provider address identifier being provided but an address is provided (step 618), the supplier account update unit 120 may also search the database 130 for an address of the particular healthcare provider based on the provided address (step 620) and may determine whether one or more matches are found (step 622).

The provided address may be a normalized or non-normalized address. The system may initially check to see if the non-normalized address is recognized. A normalized address is an address which has been formatted in a particular way, according to guidelines of the United States Postal Service (USPS). In some embodiments, the normalization may be by a governing body of the jurisdiction the address is within. If the non-normalized address is not recognized, the system normalizes the provided address information. A normalization algorithm may be provided by the governing body (e.g., USPS). Money and processing resources may be saved by initially checking for a match without normalization of the provided address. Once the provided address is normalized, the normalized address is searched for a match.

In response to multiple matches being found, the multiple matches may be shown (step 624). The multiple matches may be sorted by confidence level, as disclosed herein. The proper healthcare provider location from the results may be identified using the user interface 108 (step 626), and the database 130 may be updated (step 616). If no entry from the multiple results is the corresponding healthcare provider address, a new entry may be created in the database 130 (step 628). Alternatively, the entire process may be cancelled (step 630).

In addition, if no matches are found, a new entry may be created in the database 130 (step 628).

In response to the remove-by-omission flag being set (or true), any supplier-assigned account identifiers previously associated with the address that are not in the list of supplier-assigned account identifiers are no longer associated with the address.

The entity update unit 122 may be used to update information in the database associated with a healthcare provider. The entity update unit 122 may be accessed by other units within the system 114 or by a user via a user interface 108. The entity update unit 122 receives an identifier type, an old GPO-assigned healthcare provider identifier, a new GPO-assigned healthcare provider identifier, and a system-assigned identifier. The entity update unit 122 searches the database 130 for a match to the old GPO-assigned healthcare provider identifier and updates the database 130 with the new GPO-assigned healthcare provider identifier. The new GPO-assigned healthcare provider identifier may be stored in an entry associated with the system-assigned identifier associated with the healthcare provider.

The entity location update unit 124 may be used to update information in the database associated with a healthcare provider. The entity location update unit 124 may be accessed by other units within the system 114 or by a user via a user interface 108. The entity location update unit 124 receives, from the user interface 108, an identifier type, an old GPO-assigned healthcare provider address identifier, a new GPO-assigned healthcare provider address identifier, and a system-assigned identifier. The entity location update unit 124 searches the database 130 for a match to the old GPO-assigned healthcare provider address identifier and updates the database 130 with the new GPO-assigned healthcare provider address identifier. The new GPO-assigned healthcare provider address identifier may be stored in an entry associated with the system-assigned identifier associated with the healthcare provider.

Once the GPO contract is matched to the hospital address, the supplier may be able to identify which contracts their internal account numbers are associated with. Enabling the supplier to view the GPO contracts with their own supplier account numbers allows suppliers to better understand the GPO contracts. In addition, suppliers and healthcare providers are also able to see, on their respective user interfaces, which items are being managed within a contract. It also enables suppliers to see what contracts are in effect at the healthcare provider location, so in response to creating new account numbers, they can track what contracts are already in effect, providing a more consistent pricing experience for both the suppliers and the healthcare providers.

In some embodiments, a user-controlled parameter may exist where new healthcare providers and healthcare provider addresses are not created, and only existing healthcare providers and healthcare provider addresses are either accessed or updated.

In some embodiments, if a supplier-assigned account number is associated with a different provider, then the supplier-assigned account number will be moved to the provider specified by the user. In response to a supplier uploading a supplier-assigned account number based on an address, if the address does not already exist, it is not created.

FIG. 7 illustrates an example embodiment of a user interface 700. The user interface 700 may be used with the user interfaces 108 described herein.

User interface 700 includes fields for the user to input a healthcare provider name 702 (e.g., healthcare provider name), a GPOEntityID type 704 (e.g., type of GPO-assigned identifier), a GPOEntityID Value 706 (e.g., a GPO-assigned identifier), a phone type 708 (e.g., mobile, cell, fax, etc.), a phone number 712, an external identifier type 710 (e.g., DUNS, GLN, HIN, FEIN), an external identifier value 714, and an address 716.

A single 718 supplementing of the database 130 with the information provided in the fields 702-716 may be executed, or a bulk 720 supplementing of the database 130 may be performed. In response to a bulk 720 action being performed, a GPO roster file or supplier account file may be uploaded.

Any of the systems described herein may communicate with a smartphone, the internet and/or social networking websites. Any communication, transmission and/or channel discussed herein may include any system or method for delivering content (e.g. data, information, metadata, etc), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE® TV®, PANDORA®, XBOX®, SONY® PLAYSTATION®), a uniform resource locator ("URL"), a document (e.g., a MICROSOFT® Word® document, a MICROSOFT® Excel® document, an ADOBE®.pdf document, etc.), an "ebook," an "emagazine," an application or microapplication (as described herein), an SMS or other type of text message, an email, facebook, twitter, MMS and/or other type of communication technology. In various embodiments, a channel may be hosted or provided by a data partner. In various embodiments, the distribution channel may comprise in response to of a merchant website, a social media website, affiliate or partner websites, an external vendor, a mobile device communication, social media network and/or location based service. Distribution channels may include in response to of a merchant website, a social media site, affiliate or partner websites, an external vendor, or a mobile device communication. Examples of social media sites include FACEBOOK®, FOURSQUARE®, TWITTER®, MYSPACE®, LINKEDIN®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

In various embodiments, components, modules, and/or engines of the system may be implemented as microapplications or micro-apps. Micro-apps are typically deployed in the context of a mobile operating system, including for example, a WINDOWS® mobile operating system, an ANDROID® Operating System, APPLE® IOS®), a BLACKBERRY® operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system may communicate with any network using any data communications protocol. As used herein, the term "network" includes any cloud, cloud computing system or electronic communications system or method which incorporates hardware and/or software components. Communication among the parties may be accomplished through any suitable communication channels using any communications protocol, such as, for example, a telephone network, an extranet, an intranet, Internet, point of interaction device (point of sale device, personal digital assistant (e.g., IPHONE®, BLACKBERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE® talk, IP-6, NetBIOS®, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gove/publications/nistpubs/800-145/SP800-145.pdf (last visited June 2012), which is hereby incorporated by reference in its entirety.

The computers discussed herein may provide a suitable website or other Internet-based graphical user interface which is accessible by users. In one embodiment, the MICROSOFT® INTERNET INFORMATION SERVICES® (IIS), MICROSOFT® Transaction Server (MTS), and MICROSOFT® SQL Server, are used in conjunction with the MICROSOFT® operating system, MICROSOFT® NT web server software, a MICROSOFT® SQL Server database system, and a MICROSOFT® Commerce Server. Additionally, components such as Access or MICROSOFT® SQL Server, ORACLE®, Sybase, Informix MySQL, Interbase, etc., may be used to provide an Active Data Object (ADO) compliant database management system. In one embodiment, the Apache web server is used in conjunction with a Linux operating system, a MySQL database, and the Perl, PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® APPLE® ts, JAVASCRIPT, active server pages (ASP), common gateway interface scripts (CGI), extensible markup language (XML), dynamic HTML, cascading style sheets (CSS), AJAX (Asynchronous JAVASCRIPT And XML), helper applications, plug-ins, and the like. A server may include a web service that receives a request from a web server, the request including a URL and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

The system may also create, maintain and/or supplement a user profile. A "user profile" or "user profile data" may comprise any information or data about a consumer that describes an attribute associated with the consumer (e.g., a preference, an interest, demographic information, personally identifying information, and the like).

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like. Similarly, as used herein, "authenticate" or similar terms may include an exact authentication, a partial authentication, authenticating a subset of data, a correspondence, satisfying certain criteria, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) a transaction account and (ii) an item (e.g., offer, reward, discount) and/or digital channel. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

The disclosure and claims do not describe only a particular outcome of reconciling data, but the disclosure and claims include specific rules for implementing the outcome of reconciling data and that render information into a specific format that is then used and applied to create the desired results of reconciling data, as set forth in *McRO, Inc. v. Bandai Namco Games America Inc.* (Fed. Cir. case number 15-1080, Sep. 13, 2016). In other words, the outcome of reconciling data can be performed by many different types of rules and combinations of rules, and this disclosure includes various embodiments with specific rules. While the absence of complete preemption may not guarantee that a claim is eligible, the disclosure does not sufficiently preempt the field of reconciling data at all. The disclosure acts to narrow, confine, and otherwise tie down the disclosure so as not to cover the general abstract idea of just reconciling data. Significantly, other systems and methods exist for reconciling data, so it would be inappropriate to assert that the claimed invention preempts the field or monopolizes the basic tools of reconciling data. In other words, the disclosure will not prevent others from reconciling data, because other systems are already performing the functionality in different ways than the claimed invention. Moreover, the claimed invention includes an inventive concept that may be found in the non-conventional and non-generic arrangement of known, conventional pieces, in conformance with *Bascom v. AT&T Mobility*, 2015-1763 (Fed. Cir. 2016). The disclosure and claims go way beyond any conventionality of any one of the systems in that the interaction and synergy of the systems leads to additional functionality that is not provided by any one of the systems operating independently. The disclosure and claims may also include the interaction between multiple different systems, so the disclosure cannot be considered an implementation of a generic computer, or just "apply it" to an abstract process. The disclosure and claims may also be directed to improvements to software with a specific implementation of a solution to a problem in the software arts.

In various embodiments, the system and method may include alerting a subscriber when their computer is offline. The system may include generating customized information and alerting a remote subscriber that the information can be accessed from their computer. The alerts are generated by filtering received information, building information alerts and formatting the alerts into data blocks based upon subscriber preference information. The data blocks are transmitted to the subscriber's wireless device which, when connected to the computer, causes the computer to auto-launch an application to display the information alert and provide access to more detailed information about the information alert. More particularly, the method may comprise providing a viewer application to a subscriber for installation on the remote subscriber computer; receiving information at a transmission server sent from a data source over the Internet, the transmission server comprising a microprocessor and a memory that stores the remote subscriber's preferences for information format, destination address, specified information, and transmission schedule, wherein the microprocessor filters the received information by comparing the received information to the specified information; generates an information alert from the filtered information that contains a name, a price and a universal resource locator (URL), which specifies the location of the data source; formats the information alert into data blocks according to said information format; and transmits the formatted information alert over a wireless communication channel to a wireless device associated with a subscriber based upon the destination address and transmission schedule, wherein the alert activates the application to cause the information alert to display on the remote subscriber computer and to enable connection via the URL to the data source over the Internet when the wireless device is locally connected to the remote subscriber computer and the remote subscriber computer comes online.

In various embodiments, the system and method may include a graphical user interface for dynamically relocating/rescaling obscured textual information of an underlying window to become automatically viewable to the user. By permitting textual information to be dynamically relocated based on an overlap condition, the computer's ability to display information is improved. More particularly, the method for dynamically relocating textual information within an underlying window displayed in a graphical user interface may comprise displaying a first window containing textual information in a first format within a graphical user interface on a computer screen; displaying a second window within the graphical user interface; constantly monitoring the boundaries of the first window and the second window to detect an overlap condition where the second window overlaps the first window such that the textual information in the first window is obscured from a user's view; determining the textual information would not be completely viewable if relocated to an unobstructed portion of the first window; calculating a first measure of the area of the first window and a second measure of the area of the unobstructed portion of the first window; calculating a scaling factor which is proportional to the difference between the first measure and the second measure; scaling the textual information based upon the scaling factor; automatically relocating the scaled textual information, by a processor, to the unobscured portion of the first window in a second format during an overlap condition so that the entire scaled textual information is viewable on the computer screen by the user; and automatically returning the relocated scaled textual information, by the processor, to the first format within the first window when the overlap condition no longer exists.

In various embodiments, the system may also include isolating and removing malicious code from electronic messages (e.g., email) to prevent a computer from being compromised, for example by being infected with a computer virus. The system may scan electronic communications for malicious computer code and clean the electronic communication before it may initiate malicious acts. The system operates by physically isolating a received electronic communication in a "quarantine" sector of the computer memory. A quarantine sector is a memory sector created by the computer's operating system such that files stored in that sector are not permitted to act on files outside that sector. When a communication containing malicious code is stored in the quarantine sector, the data contained within the communication is compared to malicious code-indicative patterns stored within a signature database. The presence of a particular malicious code-indicative pattern indicates the nature of the malicious code. The signature database further includes code markers that represent the beginning and end points of the malicious code. The malicious code is then extracted from malicious code-containing communication. An extraction routine is run by a file parsing component of the processing unit. The file parsing routine performs the following operations: scan the communication for the identified beginning malicious code marker; flag each scanned byte between the beginning marker and the successive end malicious code marker; continue scanning until no further beginning malicious code marker is found; and create a new data file by sequentially copying all non-flagged data bytes into the new file, which thus forms a sanitized communication file. The new, sanitized communication is transferred to a non-quarantine sector of the computer memory. Subsequently, all data on the quarantine sector is erased. More particularly, the system includes a method for protecting a computer from an electronic communication containing malicious code by receiving an electronic communication containing malicious code in a computer with a memory having a boot sector, a quarantine sector and a non-quarantine sector; storing the communication in the quarantine sector of the memory of the computer, wherein the quarantine sector is isolated from the boot and the non-quarantine sector in the computer memory, where code in the quarantine sector is prevented from performing write actions on other memory sectors; extracting, via file parsing, the malicious code from the electronic communication to create a sanitized electronic communication, wherein the extracting comprises scanning the communication for an identified beginning malicious code marker, flagging each scanned byte between the beginning marker and a successive end malicious code marker, continuing scanning until no further beginning malicious code marker is found, and creating a new data file by sequentially copying all non-flagged data bytes into a new file that forms a sanitized communication file; transferring the sanitized electronic communication to the non-quarantine sector of the memory; and deleting all data remaining in the quarantine sector.

In various embodiments, the system may also address the problem of retaining control over customers during affiliate purchase transactions, using a system for co-marketing the "look and feel" of the host web page with the product-related content information of the advertising merchant's web page. The system can be operated by a third-party outsource provider, who acts as a broker between multiple hosts and merchants. Prior to implementation, a host places links to a merchant's webpage on the host's web page. The links are associated with product-related content on the merchant's web page. Additionally, the outsource provider system stores the "look and feel" information from each host's web pages in a computer data store, which is coupled to a computer server. The "look and feel" information includes visually perceptible elements such as logos, colors, page layout, navigation system, frames, mouse-over effects or other elements that are consistent through some or all of each host's respective web pages. A customer who clicks on an advertising link is not transported from the host web page to the merchant's web page, but instead is redirected to a composite web page that combines product information associated with the selected item and visually perceptible elements of the host web page. The outsource provider's server responds by first identifying the host web page where the link has been selected and retrieving the corresponding stored "look and feel" information. The server constructs a composite web page using the retrieved "look and feel" information of the host web page, with the product-related content embedded within it, so that the composite web page is visually perceived by the customer as associated with the host web page. The server then transmits and presents this composite web page to the customer so that she effectively remains on the host web page to purchase the item without being redirected to the third party merchant affiliate. Because such composite pages are visually perceived by the customer as associated with the host web page, they give the customer the impression that she is viewing pages served by the host. Further, the customer is able to purchase the item without being redirected to the third party merchant affiliate, thus allowing the host to retain control over the customer. This system enables the host to receive the same advertising revenue streams as before but without the loss of visitor traffic and potential customers. More particularly, the system may be useful in an outsource provider serving web pages offering commercial opportunities. The computer store containing data, for each of a plurality of first web pages, defining a plurality of visually perceptible elements, which visually perceptible elements correspond to the plurality of first web pages; wherein each of the first web pages belongs to one of a plurality of web page owners; wherein each of the first web pages displays at least one active link associated with a commerce object associated with a buying opportunity of a selected one of a plurality of merchants; and wherein the selected merchant, the outsource provider, and the owner of the first web page displaying the associated link are each third parties with respect to one other; a computer server at the outsource provider, which computer server is coupled to the computer store and programmed to: receive from the web browser of a computer user a signal indicating activation of one of the links displayed by one of the first web pages; automatically identify as the source page the one of the first web pages on which the link has been activated; in response to identification of the source page, automatically retrieve the stored data corresponding to the source page; and using the data retrieved, automatically generate and transmit to the web browser a second web page that displays: information associated with the commerce object associated with the link that has been activated, and the plurality of visually perceptible elements visually corresponding to the source page.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "in response to of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

System program instructions and/or controller instructions may be loaded onto a tangible, non-transitory, computer-readable medium (also referred to herein as a tangible, non-transitory, memory) having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method comprising:
receiving, by a computer-based system, from a first entity via a first user interface, a roster file including an organization identifier and an organization address identifier assigned by the first entity;
updating, by the computer-based system, an entry in a database associated with an organization based on the organization identifier and the organization address identifier assigned by the first entity;
receiving, by the computer-based system, from a second entity via a second user interface, an account file including an account identifier assigned by the second entity, the account identifier representing an address of the organization;
updating, by the computer-based system, the entry in the database associated with the organization based on the account identifier assigned by the second entity such that the organization address identifier assigned by the first entity is associated with the account identifier assigned by the second entity;
receiving, by the computer-based system, a signal indicating activation of a link displayed by a first web page;
automatically identifying, by the computer-based system, the first web page as a source page;
in response to identification of the source page, automatically retrieving, by the computer-based system, stored data corresponding to the source page; and
using the data retrieved, automatically generating and transmitting, by the computer-based system and to a web browser, a second web page that displays the organization address identifier associated with the account identifier associated with the link that has been activated, and a plurality of visually perceptible elements visually corresponding to the source page.

2. The method of claim 1, wherein the updating the entry associated with the organization based on the organization identifier and the organization address identifier assigned by the first entity further comprises:
searching, by the computer-based system, the database to determine whether the database includes the entry associated with the organization identifier assigned by the first entity; and
updating, by the computer-based system, the entry with the organization address identifier assigned by the first entity.

3. The method of claim 1,
wherein the roster file further includes secondary information associated with the organization, and
wherein the updating the entry associated with the organization based on the organization identifier and the organization address identifier assigned by the first entity further comprises:
searching, by the computer-based system, the database to determine whether the database includes an entry associated with the secondary information associated with the organization, and
updating, by the computer-based system, the entry with the organization address identifier assigned by the first entity in response to the secondary information matching a single entry.

4. The method of claim 1,
wherein the roster file further includes secondary information associated with the organization, and
wherein the updating the entry associated with the organization based on the organization identifier and the organization address identifier assigned by the first entity further comprises:
searching, by the computer-based system, the database to determine whether the database includes an entry associated with the secondary information associated with the organization,
displaying, by the computer-based system, on the first user interface, a listing of a plurality of entries in response to the secondary information matching more than one entry,
receiving, by the computer-based system, from the first user interface, an identification of a matching entry from the listing of the plurality of entries, and
updating, by the computer-based system, the matching entry with the organization address identifier assigned by the first entity.

5. The method of claim 1,
wherein the roster file further includes secondary information associated with the organization, and
wherein the updating the entry associated with the organization based on the organization identifier and the organization address identifier assigned by the first entity further comprises:
searching, by the computer-based system, the database to determine whether the database includes an entry associated with the secondary information associated with the organization, and
creating, by the computer-based system, an entry with the organization address identifier assigned by the first entity in response to the secondary information matching no entries in the database.

6. The method of claim 1, wherein the updating the entry associated with the organization based on the organization identifier and the organization address identifier assigned by the first entity further comprises:
searching, by the computer-based system, the database to determine whether the database includes an entry associated with the organization address identifier assigned by the first entity, and
updating, by the computer-based system, the entry with the organization identifier assigned by the first entity.

7. The method of claim 1, wherein the updating the entry associated with the organization based on the organization identifier and the organization address identifier assigned by the first entity further comprises:
searching, by the computer-based system, the database to determine whether the database includes an entry associated with the organization address identifier assigned by the first entity,
searching, by the computer-based system, the database to determine whether the database includes an entry associated with a standardized address, and
updating, by the computer-based system, the entry with an organization location identifier assigned by the first entity in response to the database including the entry associated with the standardized address.

8. The method of claim 1,
wherein the account file received from the second entity is a cross-listing file indicating a corresponding organization identifier or the organization address identifier for the account identifier, and
wherein the updating the entry associated with the organization based on the account identifier assigned by the second entity further comprises:

searching, by the computer-based system, the database to determine whether the database includes an entry associated with the corresponding organization identifier or the organization address identifier; and updating, by the computer-based system, the entry with the account identifier assigned by the second entity in response to the database including the entry associated with the corresponding organization identifier or the organization address identifier.

9. The method of claim 1, wherein the organization identifier represents an organization name and the organization address identifier represents the address of the organization.

10. The method of claim 1, further comprising accessing, by the computer-based system, contract details associated with a contract.

11. The method of claim 1, further comprising accessing, by the first user interface through a connection with the computer-based system, contract details associated with a contract.

12. The method of claim 1, further comprising displaying, by the computer-based system, on the first user interface, the organization address identifier assigned by the first entity.

13. The method of claim 1, further comprising accessing, by the second user interface through a connection with the computer-based system, contract details associated with a contract.

14. The method of claim 1, further comprising displaying, by the computer-based system, on the second user interface, the account identifier assigned by the second entity.

15. The method of claim 1, further comprising reconciling conflicting of the organization identifier and the organization address identifier from the first entity and the second entity.

16. The method of claim 1, wherein the first entity and the second entity are associated with a contract for items to be delivered to the address of the organization based on the organization address identifier.

17. The method of claim 1, wherein the entry is associated with a contract between the first entity and the second entity.

18. The method of claim 1, wherein the first entity is a group purchasing organization (GPO) and the second entity is a supplier.

19. An article of manufacture including a non-transitory, tangible computer readable storage medium having instructions stored thereon that, in response to execution by a computer-based system, cause the computer-based system to perform operations comprising:

receiving, by the computer-based system, from a first entity via a first user interface, a roster file including an organization identifier and an organization address identifier assigned by the first entity;

updating, by the computer-based system, an entry in a database associated with an organization based on the organization identifier and the organization address identifier assigned by the first entity;

receiving, by the computer-based system, from a second entity via a second user interface, an account file including an account identifier assigned by the second entity, the account identifier representing an address of the organization;

updating, by the computer-based system, the entry in the database associated with the organization based on the account identifier assigned by the second entity such that the organization address identifier assigned by the first entity is associated with the account identifier assigned by the second entity;

receiving, by the computer-based system, a signal indicating activation of a link displayed by a first web page;

automatically identifying, by the computer-based system, the first web page as a source page;

in response to identification of the source page, automatically retrieving, by the computer-based system, stored data corresponding to the source page; and using the data retrieved, automatically generating and transmitting, by the computer-based system and to a web browser, a second web page that displays the organization address identifier associated with the account identifier associated with the link that has been activated, and a plurality of visually perceptible elements visually corresponding to the source page.

20. A system comprising:

a processor; and a tangible, non-transitory memory configured to communicate with the processor, the tangible, non-transitory memory having instructions stored thereon that, in response to execution by the processor, cause the processor to perform operations comprising:

receiving, by the processor, from a first entity via a first user interface, a roster file including an organization identifier and an organization address identifier assigned by the first entity;

updating, by the processor, an entry in a database associated with an organization based on the organization identifier and the organization address identifier assigned by the first entity;

receiving, by the processor, from a second entity via a second user interface, an account file including an account identifier assigned by the second entity, the account identifier representing an address of the organization;

updating, by the processor, the entry in the database associated with the organization based on the account identifier assigned by the second entity such that the organization address identifier assigned by the first entity is associated with the account identifier assigned by the second entity;

receiving, by the processor, a signal indicating activation of a link displayed by a first web page;

automatically identifying, by the processor, the first web page as a source page;

in response to identification of the source page, automatically retrieving, by the computer-based system, stored data corresponding to the source page; and using the data retrieved, automatically generating and transmitting, by the processor and to a web browser, a second web page that displays the organization address identifier associated with the account identifier associated with the link that has been activated, and a plurality of visually perceptible elements visually corresponding to the source page.

\* \* \* \* \*